United States Patent
Brueck et al.

(10) Patent No.: US 8,940,757 B2
(45) Date of Patent: Jan. 27, 2015

(54) PRASUGREL IN MICRONIZED, CRYSTALLINE FORM AND PHARMACEUTICAL COMPOSITION THEREOF

(75) Inventors: Sandra Brueck, Munich (DE); Jana Paetz, Bonn (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 13/578,443

(22) PCT Filed: Feb. 10, 2011

(86) PCT No.: PCT/EP2011/051988
§ 371 (c)(1),
(2), (4) Date: Oct. 15, 2012

(87) PCT Pub. No.: WO2011/098536
PCT Pub. Date: Aug. 18, 2011

(65) Prior Publication Data
US 2013/0035355 A1    Feb. 7, 2013

(30) Foreign Application Priority Data
Feb. 11, 2010 (EP) .................................. 10153348

(51) Int. Cl.
*C07D 495/04* (2006.01)
*A61K 9/16* (2006.01)
*A61K 9/20* (2006.01)
*A61K 9/14* (2006.01)

(52) U.S. Cl.
CPC ............ *C07D 495/04* (2013.01); *A61K 9/1652* (2013.01); *A61K 9/2018* (2013.01); *A61K 9/2027* (2013.01); *A61K 9/2054* (2013.01); *A61K 9/146* (2013.01)
USPC ........................... 514/301; 428/402; 546/114

(58) Field of Classification Search
None
See application file for complete search history.

(56) References Cited

U.S. PATENT DOCUMENTS

2009/0281136 A1* 11/2009 Mhetre et al. ................. 514/301

FOREIGN PATENT DOCUMENTS

| EP | 2100607 A1 * | 9/2009 |
|----|---|---|
| EP | 2100608 A1 | 9/2009 |
| EP | 2100610 A1 | 9/2009 |
| EP | 2275087 * | 1/2011 |
| WO | WO 2009/122440 | 10/2009 |
| WO | WO 2009/130289 | 10/2009 |
| WO | WO 2011/004392 A1 * | 1/2011 |

OTHER PUBLICATIONS

Prasugrel MSDS [online] LC laboratories 2010 [Retrieved on Mar. 1, 2014] Retrieved from the internet <URL http://www.lclabs.com/MSDS/P-6866MSDS.php4.*

* cited by examiner

*Primary Examiner* — Melenie McCormick
*Assistant Examiner* — Taina D Matos Negron
(74) *Attorney, Agent, or Firm* — Chalin Smith; Smith Patent

(57) ABSTRACT

The present invention relates to Prasugrel or a pharmaceutically acceptable salt thereof, compositions containing said active ingredient as well as pharmaceutical compositions containing said active ingredient or a composition containing said active ingredient. The present invention further relates to methods for the preparation of the novel compositions.

16 Claims, 11 Drawing Sheets

PRASUGREL IN MICRONIZED, CRYSTALLINE FORM AND PHARMACEUTICAL COMPOSITION THEREOF

This application corresponds to the national phase of International Application No. PCT/EP2011/051988 filed Feb. 10, 2011, which, in turn, claims priority to European Patent Application No. 10.153348.7 filed Feb. 11, 2010, the contents of which are incorporated by reference herein in their entirety.

The present invention relates to Prasugrel or a pharmaceutically acceptable salt thereof, compositions containing said active ingredient as well as pharmaceutical compositions containing said active ingredient or a composition containing said active ingredient. The present invention further relates to methods for the preparation of the novel compositions.

Prasugrel has the chemical name 2-acetoxy-5-(α-cyclopropylcarbonyl-2-fluorobenzyl)-4,5,6,7-tetrahydrothieno[3,2-c]pyridine. Prasugrel has the following structural formula:

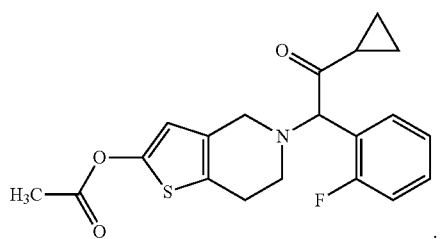 [SMILES: CC(=O)Oc1cc2c(s1)CCN(C(C(=O)C1CC1)c1ccccc1F)C2]

A method for the preparation of crystalline Prasugrel is disclosed in EP-A-0 542 411.

Various acid addition salts of Prasugrel are disclosed in EP-A-1 298 132. These are also crystalline salts.

Prasugrel is administered orally as platelet aggregation inhibitor. The problem here is that Prasugrel is a sparingly soluble active ingredient. The free base of the active ingredient has a solubility of 57 μg/ml in water, but also the salts exhibit only a limited solubility.

The solubility of an active ingredient can often be increased by micronization of the active ingredient particles. However, due to the high sensitivity to oxidation of Prasugrel direct dry milling in the μm range is not possible, since conditional on both the mechanical and thermal influence in combination with the surface enlargement here the chemical degradation is to high.

In addition, Prasugrel also has a strongly pH-dependent degradation. With pH values of <3 a degradation of more than 1% is observed already after 2 hours. This limits the potential excipients in the preparation of pharmaceutical formulations.

In the prior art, various proposals have been made to improve the solubility of Prasugrel from pharmaceutical compositions and to increase the storage stability of the respective pharmaceutical compositions. WO 2008/072535 suggests processing Prasugrel together with a low-substituted hydroxypropylcellulose into pharmaceutical compositions. For that, the active ingredient is intensely mixed with low-substituted hydroxypropylcellulose, hydroxypropylcellulose, and lactose for 3 minutes. To the obtained mixture magnesium stearate is added and the mixture is mixed again. The obtained powder is compressed to tablets. Here, Prasugrel and hydroxypropylcellulose are mixed in the ratio of about 1:1. The micronization of the active ingredient during the mixing process is not reported.

Similar pharmaceutical compositions containing in addition to Prasugrel water-soluble polymers such as hydroxypropylcellulose, hydroxypropylmethylcellulose and sodium carboxymethylcellulose are disclosed in WO 2008/069262, WO 2008/072532, and WO 2008/072534.

WO 2008/072533 discloses Prasugrel-containing pharmaceutical compositions containing in addition to the active ingredient hydroxypropylcellulose in a weight ratio of about 1:1.5. On that occasion, the mixtures are mixed for 3 minutes under high energy input in a Henschel mixer. In the given comparison example an appropriate mixture is mixed for 30 minutes in a diffusion mixer. Also here, no micronization of the active ingredient takes place.

To increase the storage stability of Prasugrel-containing tablets WO 2008/073759 suggests packaging them in an air and moisture tight container under a positive liquid gas pressure.

Thus, there is still a need for Prasugrel-containing formulations providing the active ingredient in a form as soluble as possible. In this context, there is also a need for the improvement of the dissolution rate as well as the bioavailability of the active ingredient. Moreover, it is desired to improve the chemical stability of the active ingredient, in particular to oxidative and hydrolytic degradation as well as with thermal load. A further problem consists in the improvement of the processability of Prasugrel into pharmaceutical compositions, the lowering of the hygroscopicity of the composition as well as the improvement of the storage stability of appropriate compositions.

It has now surprisingly been found that Prasugrel can be transferred to a micronized, crystalline form under particular processing conditions, wherein said micronized, crystalline form or compositions containing said form, respectively, solve one or more of the above-mentioned problems.

Thus, the present invention relates to Prasugrel or a pharmaceutically acceptable salt thereof in a micronized, crystalline form.

By crystalline form herein is meant any form of the active ingredient or its pharmaceutically acceptable salt that is essentially free and preferably entirely free of amorphous portions of the active ingredient or its pharmaceutically acceptable salt. By essentially free of crystalline portions here is meant that the form contains less than 10% by weight, preferably less than 5% by weight, and most preferably less than 1% by weight active ingredient in an amorphous form, wherein the weight percentages relate to the total amount of Prasugrel or a pharmaceutically acceptable salt thereof.

Crystalline portions of a present active ingredient may be characterized for example by DSC measurement and IR spectroscopy.

The crystalline form can be distinguished from the non-crystalline form of the active ingredient for example also by IR spectroscopy. FIG. 1 shows the IR spectrum of crystalline Prasugrel. FIG. 2 shows the IR spectrum of amorphous Prasugrel. In addition to a shift of the peaks for the amorphous active ingredient there can be seen an additional peak at about 1778 $cm^{-1}$ and for the crystalline Prasugrel additionally peaks at about 1254 $cm^{-1}$, and about 830 $cm^{-1}$. Moreover, the bands of the IR spectra are summarized in the following table 1 (for FIG. 1) and 2 (for FIG. 2).

TABLE 1

| Wave Number [cm⁻¹] | Transmission [%] | Wave Number [cm⁻¹] | Transmission [%] | Wave Number [cm⁻¹] | Transmission [%] | Wave Number cm⁻¹ | Transmission [%] | Wave Number cm⁻¹ | Transmission [%] |
|---|---|---|---|---|---|---|---|---|---|
| 2922.8 | 92.9 | 2817.9 | 93.0 | 2768.0 | 90.9 | 1756.3 | 58.3 | 1702.5 | 49.2 |
| 1612.8 | 92.8 | 1586.1 | 81.7 | 1487.3 | 64.1 | 1459.0 | 76.9 | 1444.4 | 79.3 |
| 1419.0 | 83.9 | 1388.6 | 78.7 | 1367.5 | 71.7 | 1353.2 | 82.9 | 1318.8 | 90.4 |
| 1279.2 | 88.6 | 1253.6 | 73.4 | 1233.4 | 69.3 | 1216.3 | 52.9 | 1191.5 | 30.9 |
| 1127.1 | 57.0 | 1090.0 | 69.5 | 1066.6 | 58.3 | 1049.0 | 62.6 | 1030.2 | 66.1 |
| 1008.7 | 46.1 | 978.1 | 71.2 | 952.7 | 86.9 | 925.8 | 74.2 | 887.7 | 59.3 |
| 829.5 | 59.3 | 801.6 | 59.9 | 757.4 | 42.2 | 733.1 | 69.8 | 694.9 | 76.9 |
| 662.5 | 65.0 | | | | | | | | |

TABLE 2

| Wave Number [cm⁻¹] | Transmission [%] | Wave Number [cm⁻¹] | Transmission [%] | Wave Number [cm⁻¹] | Transmission [%] | Wave Number [cm⁻¹] | Transmission [%] | Wave Number [cm⁻¹] | Transmission [%] |
|---|---|---|---|---|---|---|---|---|---|
| 2917.1 | 94.4 | 2841.6 | 93.8 | 1777.9 | 74.7 | 1758.6 | 70.0 | 1698.3 | 64.2 |
| 1612.7 | 92.2 | 1584.8 | 84.2 | 1487.3 | 65.6 | 1455.6 | 79.1 | 1418.4 | 84.1 |
| 1370.2 | 60.6 | 1176.8 | 36.7 | 1122.0 | 50.9 | 1085.3 | 66.2 | 1046.0 | 72.0 |
| 1012.9 | 52.5 | 895.4 | 69.1 | 838.1 | 79.1 | 805.2 | 66.2 | 758.0 | 39.8 |
| 693.7 | 85.8 | 671.0 | 78.2 | | | | | | |

Furthermore, the crystalline base in the DSC shows a sharp peak at 123° C. An example for this is represented in FIG. 6.

Herein, by "active ingredient" is meant Prasugrel or a pharmaceutically acceptable salt thereof. Suitable as pharmaceutically acceptable salts are for example the hydrochloride, hydrobromide, sulphate, phosphate, alkylsulphonic acid salts, such as methane sulphonate, trifluoromethane sulphonate, and ethane sulphonate, arylsulphonic acid salts, such as benzene sulphonate, p-toluene sulphonate, 1-naphthalene sulphonate, 2-naphthalene sulphonate, and 1,5-naphthalene disulphonate, as well as salts of organic acids, such as acetate, malate, fumarate, succinate, citrate, ascorbate, tartrate, oxalate, and maleate. Preferably, the active ingredient according to the present invention is the Prasugrel base.

According to the invention it was surprisingly found that Prasugrel or a pharmaceutically acceptable salt thereof can be recovered in a micronized, crystalline form by certain manufacturing methods. For example, the active ingredient together with a hydrophilic polymer can be processed in a milling process and thus micronized. It is assumed, that the presence of the hydrophilic polymer reduces the degradation of the active ingredient during milling. The active ingredient together with the hydrophilic polymer can be micronized for example by means of a dry milling method or by wet milling. In both methods it has proven to be important that only few amounts of polymer are present to stabilize the crystalline state of the active ingredient and prevent amorphization. In addition, active ingredient and polymer must be intimately mixed so that the active ingredient in the micronized form does not agglomerate again to bigger active ingredient particles. Suitable manufacturing methods are described in more detail below.

In order to provide an amount of polymer that is sufficient to reduce the decomposition of the active ingredient and at the same time prevent the agglomeration of the micronized active ingredient particles the weight ratio of Prasugrel based on the free base to hydrophilic polymer should be >1:4, preferably >1:1, preferably ≥2:1, more preferably ≥5:1. Preferable weight ratios of Prasugrel to hydrophilic polymer are for example about 4:1 or about 5:1. When in milling further polymer is added, for example at a ratio of active ingredient to hydrophilic polymer of <1:4, then a composition is obtained wherein the active ingredient is amorphous.

Polymer:

Suitable hydrophilic polymers are water soluble polymers, for example polymers having a water solubility at room temperature of >0.01 mg/ml. One or more hydrophilic polymers together with the active ingredient can be processed to the compositions according to the invention. Moreover, if desired the compositions can contain further pharmaceutically acceptable excipients.

In general, the designation "hydrophilic polymer" comprises polymers having polar groups. Examples for polar groups are hydroxy, amino, carboxy, carbonyl, ethers, esters, sulphonates. Particularly preferred are hydroxy groups.

Typically, the hydrophilic polymer has a molecular weight in the range between 1000 and 250,000 g/mol, preferably 2000 to 100,000 g/mol, and particularly preferably between 4000 and 50,000 g/mol. Further, a 2% by weigh solution of the hydrophilic polymer in pure water preferably has a viscosity between 2 and 8 mPas at 25° C. The viscosity is determined according to the European Pharmacopoeia (Ph. Eur.), 6$^{th}$ edition, section 2.2.10.

Furthermore, the hydrophilic polymer preferably has a glass transition temperature (Tg) between 20° C. and 150° C., preferably 25° C. to 100° C. The glass transition temperature (Tg) is the temperature at which the hydrophilic polymer becomes brittle at cooling and soft at heating. That means that the hydrophilic polymer becomes soft above the glass transition temperature and can be plastically deformed without breaking. The glass transition temperature is determined by means of a Mettler-Toledo® DSC 1, wherein a heating rate of 10° C./min and a cooling rate of 15° C./min are used.

For example, the hydrophilic polymer can be selected from the group consisting of cellulosederivatives, such as hydroxypropylmethylcellulose, hydroxypropylcellulose, carboxymethylcellulose, preferably as sodium or calcium salt, hydroxyethylcellulose, polyvinylpyrrolidone, preferably having a molecular weight of from 10,000 to 60,000 g/ml, copolymers of polyvinylpyrrolidone, preferably copolymers comprising vinylpyrrolidone and vinylacetate units (e.g. Povidon, VA64, BASF), preferably having a molecular weight between 40,000 and 70,000 g/ml, polyoxyethylene alkylether, polyethylene glycol, co-block polymers of ethylene oxide and propylene oxide (Poloxamer, Pluronic), polymethacrylate derivatives, polyvinyl alcohol, polyvinyl alcohol derivatives and polyethylene glycol derivatives, such as macrogol glycerol stearate. Preferred hydrophilic polymers are macrogol glycerol stearate, block copolymers of ethylene oxide and propylene oxide, polyethylene glycol, and hydroxypropylmethylcellulose.

Micronization/Particle Size Distribution:

The active ingredient Prasugrel or a pharmaceutically acceptable salt thereof are present in a micronized form in the pharmaceutical composition. That means, that the volume-weighted average particle diameter D50 is between 0.1 and 10 µm, preferably between 0.1 and 5 µm, and the D90 is between 0.2 and 20 µm, preferably between 0.2 and 16 µm.

The determination of the particle size is carried out in accordance to the European Pharmacopoeia (Ph. Eur.), $6^{th}$ edition, section 2.9.31, preferably with a Mastersizer 2000 by Malvern Instruments. The evaluation is carried out by the Fraunhofer model.

Milling Process:

The micronized, crystalline form of the active ingredient can be obtained by means of a milling process in the presence of the hydrophilic polymer. The milling can be dry or wet milling. The milling step can be followed by further processing steps, such as for example lyophilization, spray drying, or granulation onto a carrier.

In addition to the weight ratio of active ingredient to hydrophilic polymer already described above sufficiently long milling of the active ingredient polymer mixture is required to micronize the active ingredient without transferring it into the amorphous form. A suitable period can be determined by the skilled person in that whether the employed crystalline active ingredient is present in the desired particle size distribution after the milling step. If necessary, the period of the milling step may be extended. As a rule, milling of at least 30 min, preferably at least 1 h results in the desired micronization of the active ingredient.

Wet milling may be carried out e.g. in an Ultraturrax at revolutions between 11,000 and 24,000 rounds per minute, preferably about 11,000 rounds per minute.

Alternatively, wet milling may be carried out in a Netsch mill (e.g., Netsch Micro Cer). Here, a particular fine and narrow particle size distribution can be achieved.

When the milling step is dry milling then this takes place for example in a ball mill, optionally under cooling, for example by means of liquid nitrogen.

Preferably suitable for dry milling is an air jet mill, such as e.g., a 50 AS by Hosokava Alpine, wherein the pressure of the injector gas is between 2 and 8 bar, preferably at about 5 bar, and the milling gas has a pressure between 0.5 and 5 bar, preferably about 2 bar.

Spray drying subsequent to wet milling can be carried out e.g. in a Büchi B290.

In addition to the one or more hydrophilic polymers the composition according to the invention can in its preparation by milling contain further pharmaceutically acceptable excipients. Particularly suitable are for example emulsifying agents, in particular having an HLB value >12. Especially suitable for this is SDS (sodium lauryl sulphate). Amount and type of the employed hydrophilic polymers and other excipients influence the release and stabilization of the micronized, crystalline form of the active ingredient.

Thus, the present invention also relates to a method for the preparation of a composition described above comprising dry or wet milling of Prasugrel or a pharmaceutically acceptable salt thereof in the presence of the hydrophilic polymer. When the milling step is dry milling then this can be carried out under cooling, for example by means of liquid nitrogen. In a preferred embodiment milling is carried out by means of an air jet mill.

Moreover, the present invention relates to a composition obtained by the method described above.

Pharmaceutical Composition:

The above described active ingredient in micronized, crystalline form and the above describes compositions, respectively can subsequently be processed by using further pharmaceutically acceptable excipients to pharmaceutical compositions, in particular for the platelet aggregation inhibition. The finished administration forms can be e.g. tablets, capsules, sachets, or powders.

In addition to the hydrophilic polymer the pharmaceutical composition can contain one or more further pharmaceutical acceptable excipients, such as e.g., fillers, lubricants, flow control agents, release agents, disintegrants ("Lexikon der Hilfsstoffe für Pharmazie, Kosmetik and angrenzende Gebiete", edited by H. P. Fiedler, $4^{th}$ edition, and "Handbook of Pharmaceutical Excipients", $3^{rd}$ edition, edited by Arthur H. Kibbe, American Pharmaceutical Association, Washington, USA and Pharmaceutical Press, London).

Fillers: The pharmaceutical composition can contain one or more fillers. In general, a filler is a substance increasing the bulk volume of the mixture and thus the size of the resulting dosage form. Preferred examples for fillers are lactose, microcrystalline cellulose (e.g., Avicel) and calcium hydrogenphosphate. The filler may be present in an amount of 0 to 90% by weight, preferably between 25 and 85% by weight of the total weight of the composition.

Lubricants: The function of the lubricant is to ensure that the pelletizing and the ejection take place without much friction between the solids and the walls. Preferably, the lubricant is an alkaline-earth metal stearate, such as magnesium stearate, or a fatty acid, such as stearic acid. Typically, the lubricant is present in an amount of 0 to 2% by weight, preferably between 0.5 and 1.5% by weight of the total weight of the pharmaceutical composition.

Disintegrants: Usually, by a disintegrant is meant a substance that is capable of breaking up the tablet into smaller pieces as soon as it is in contact with a liquid. Preferred disintegrant are croscarmellose sodium, sodium carboxymethyl starch, cross-linked polyvinylpyrrolidone (Crospovidon) or sodium carboxymethyl glycolate (e.g. Explotab) and sodium bicarbonate. Typically, the blasting agent is present in an amount of 0 to 20% by weight, preferably between 1 and 15% by weight of the total weight of the composition.

Flow control agents: As the flow control agent there can be used e.g. colloidal silica. Preferably the flow control agent is present in an amount of 0 to 8% by weight, more preferably in an amount between 0.1 and 3% by weight of the total weight of the composition.

Stabilizers/Antioxidants: As stabilizers and antioxidants there can be used ascorbic acid and ascorbate, EDTA and its salts, citric acid and citrates, butylated hydroxyanisole, butyl hydroxy toluene or vitamin E. Preferably vitamin E is used as stabilizer.

Figure 1:
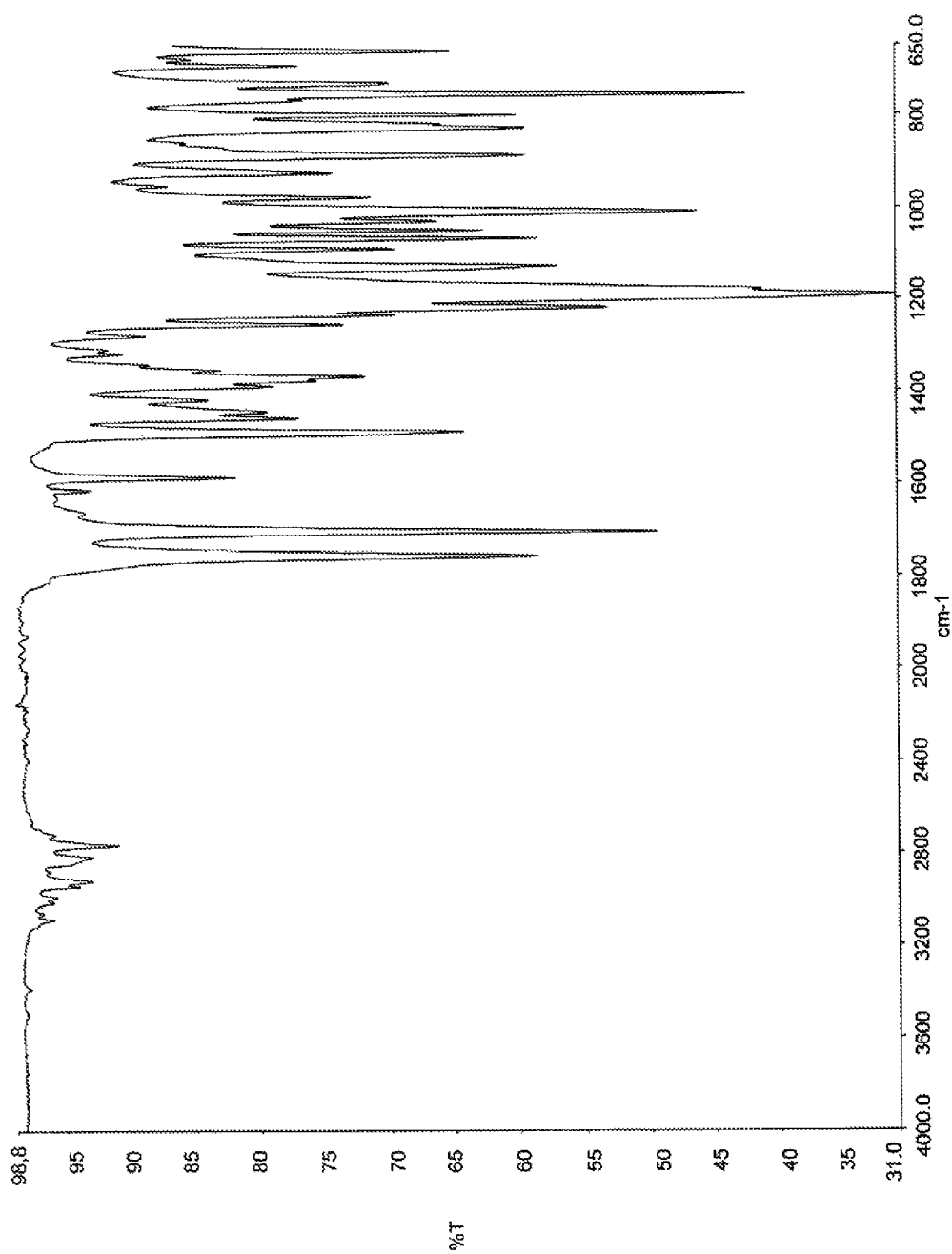
FIG. 1 shows the IR spectrum of crystalline Prasugrel.
Figure 2:
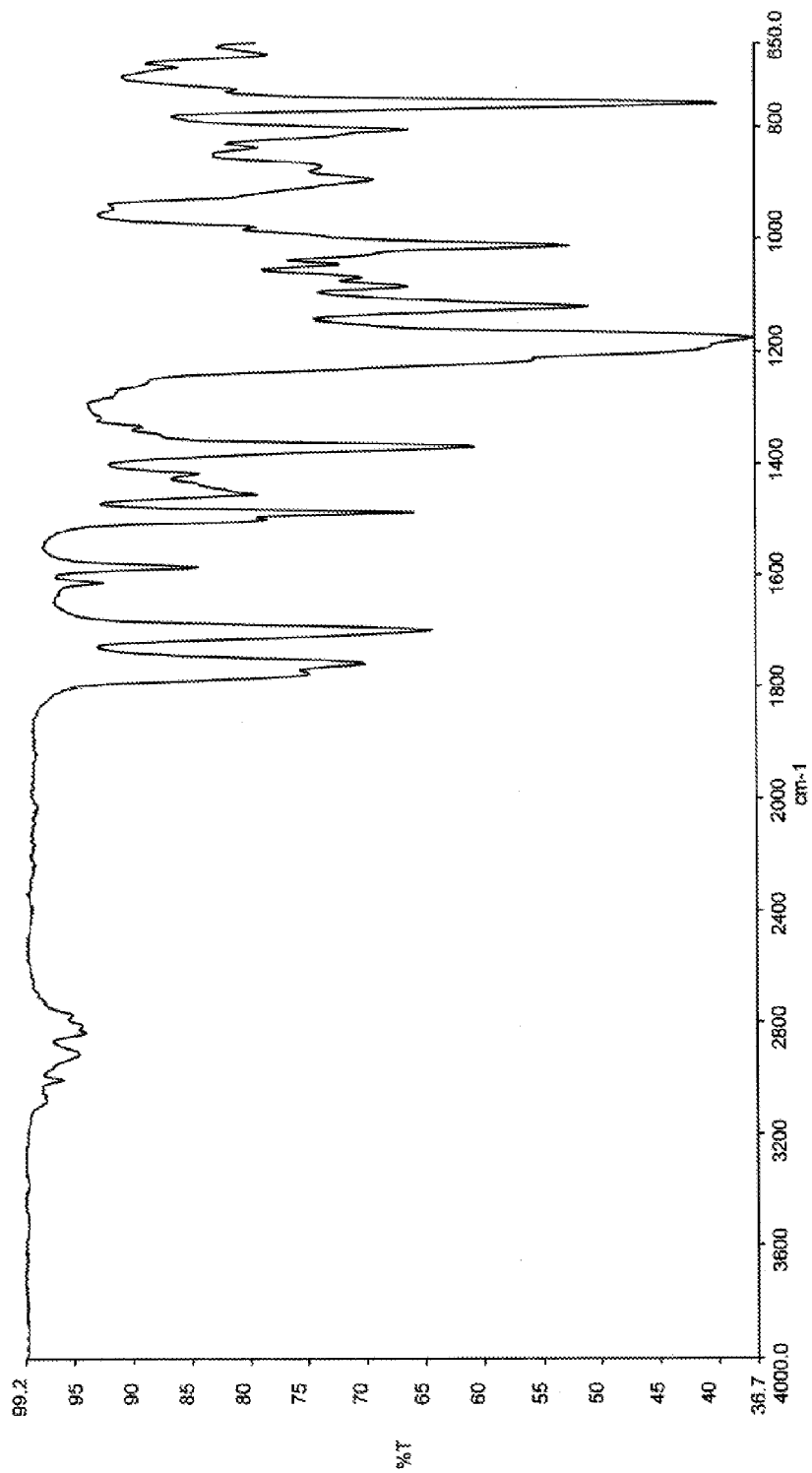
FIG. 2 shows the IR spectrum of amorphous Prasugrel.
Figure 3:
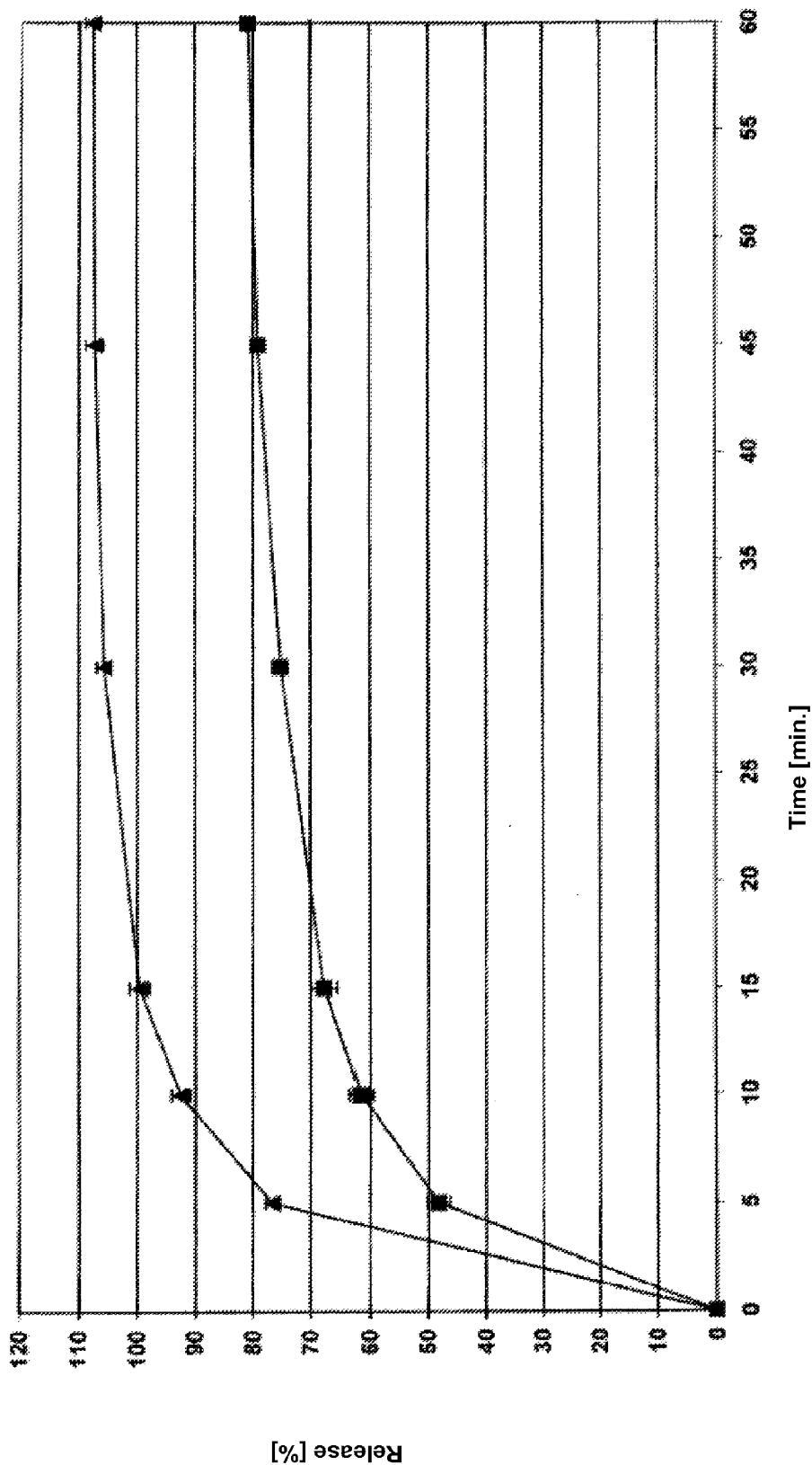
Figure 4:
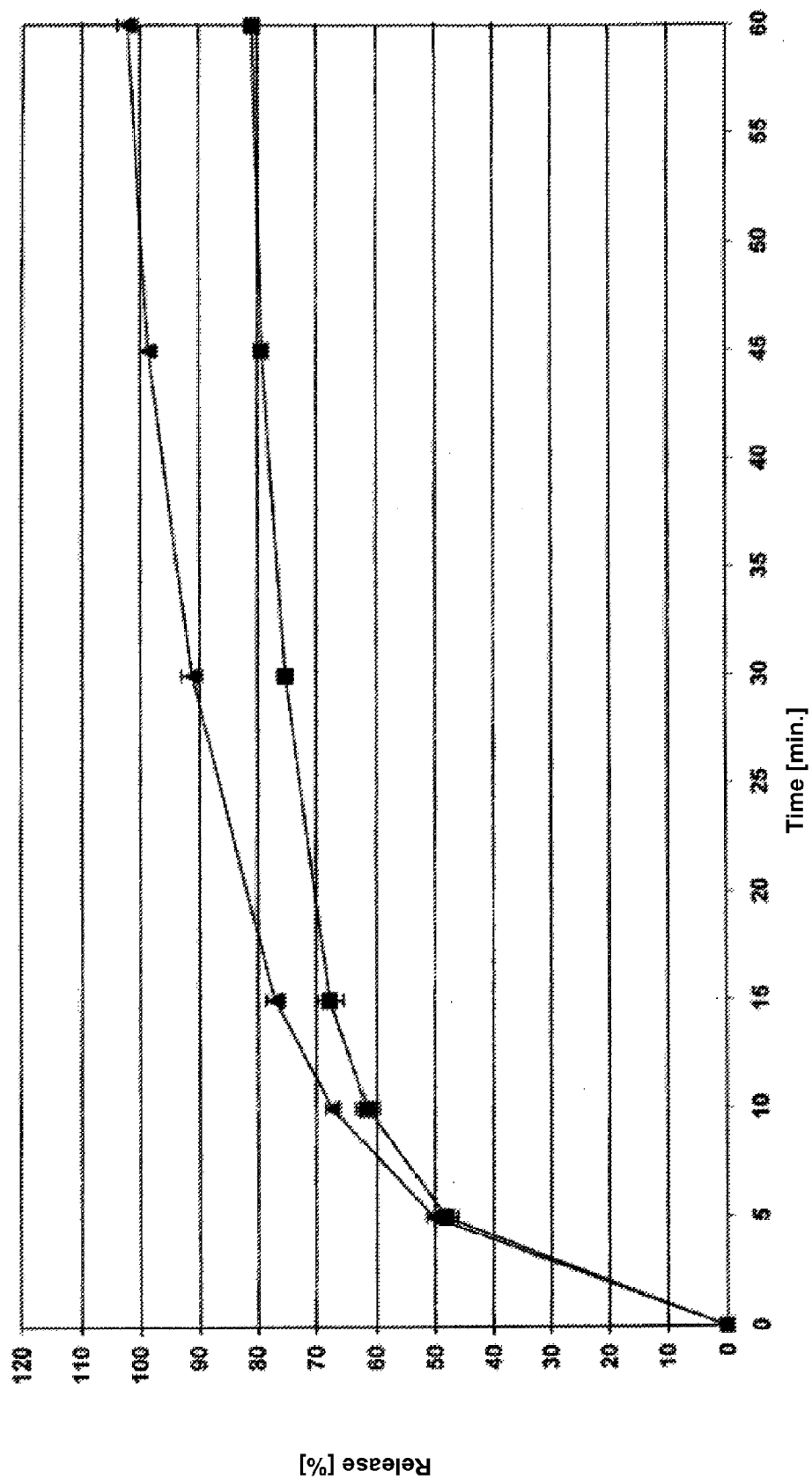
Figure 5:
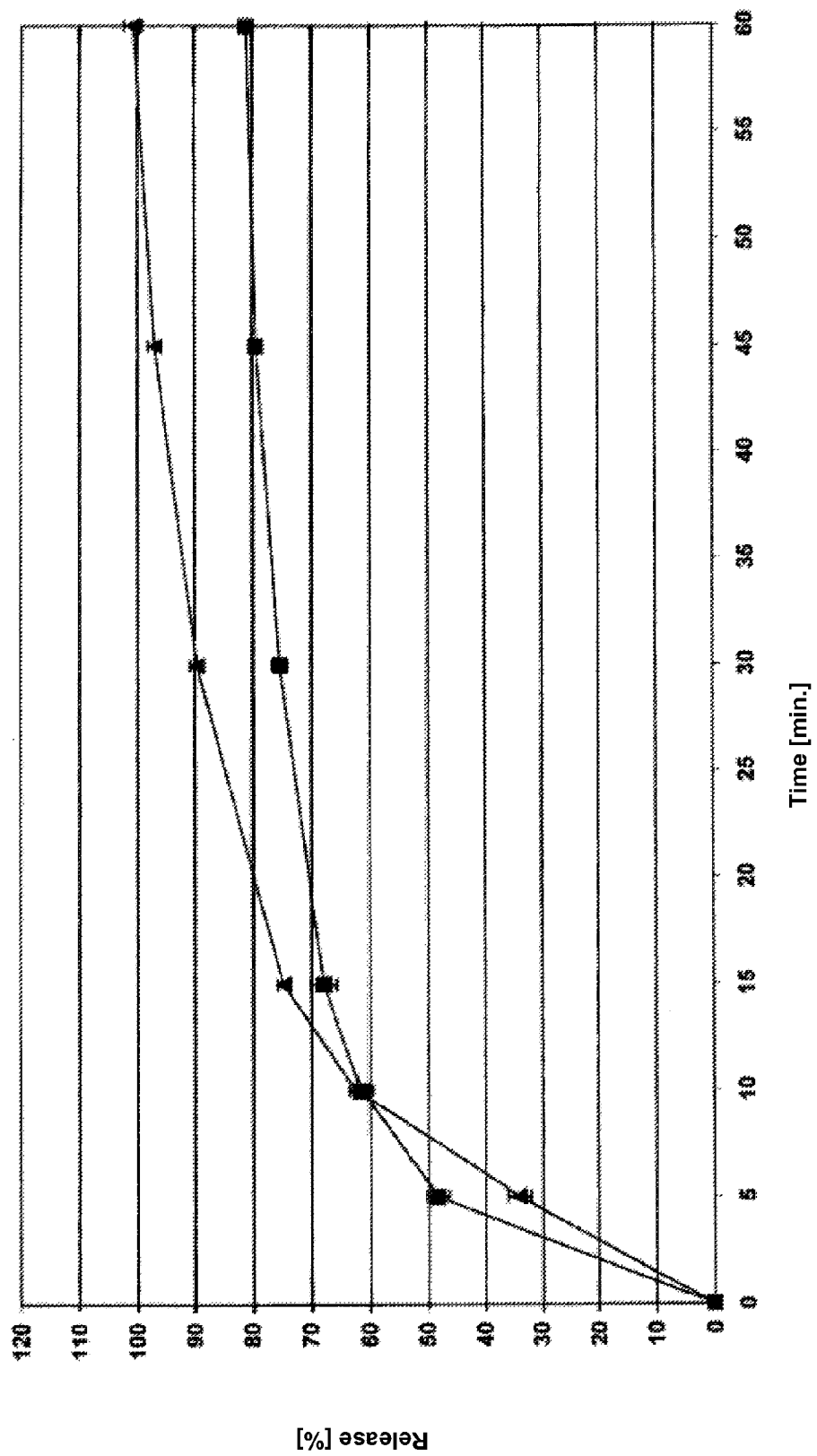
Figure 6:
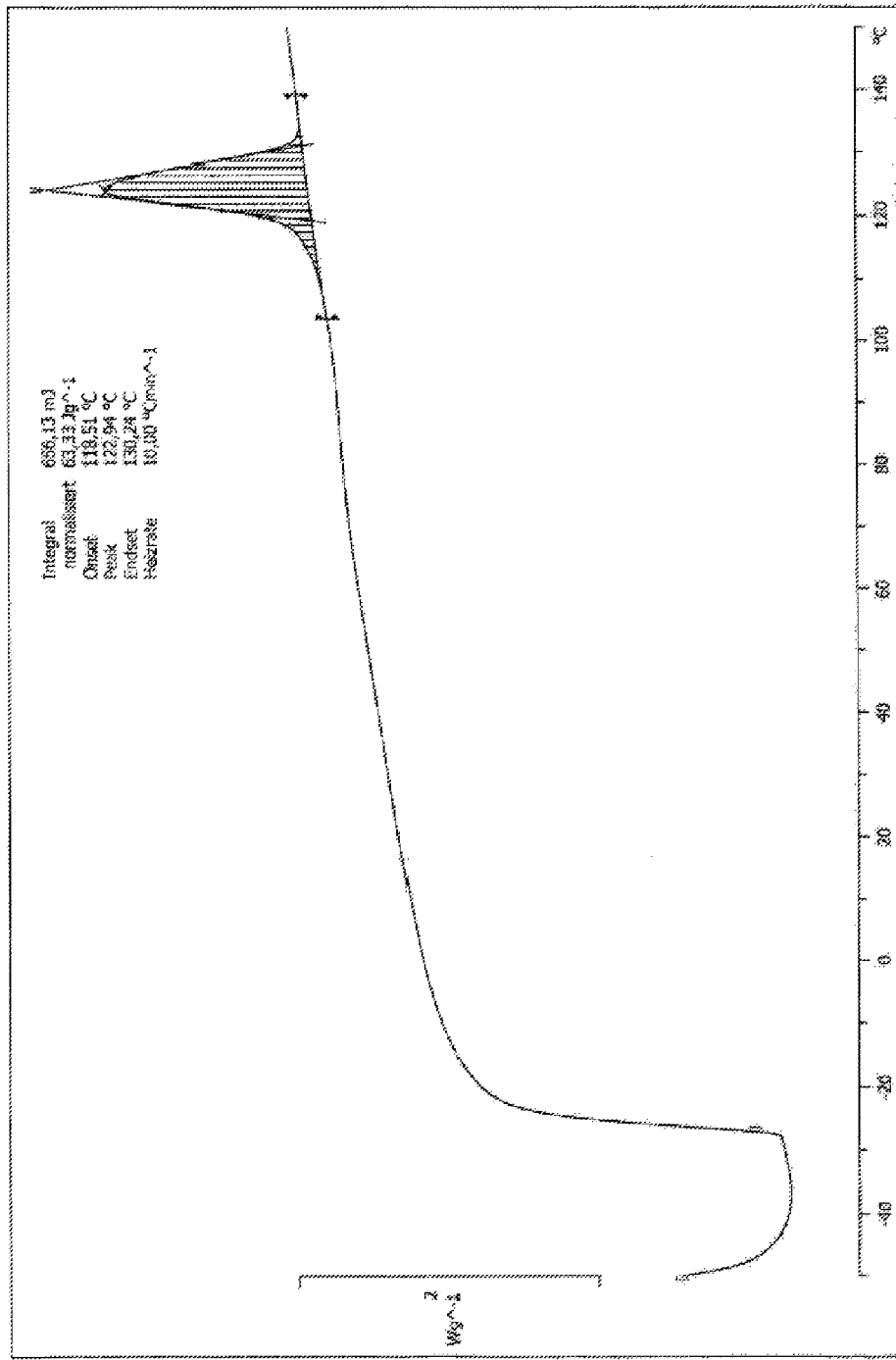
Figure 7:
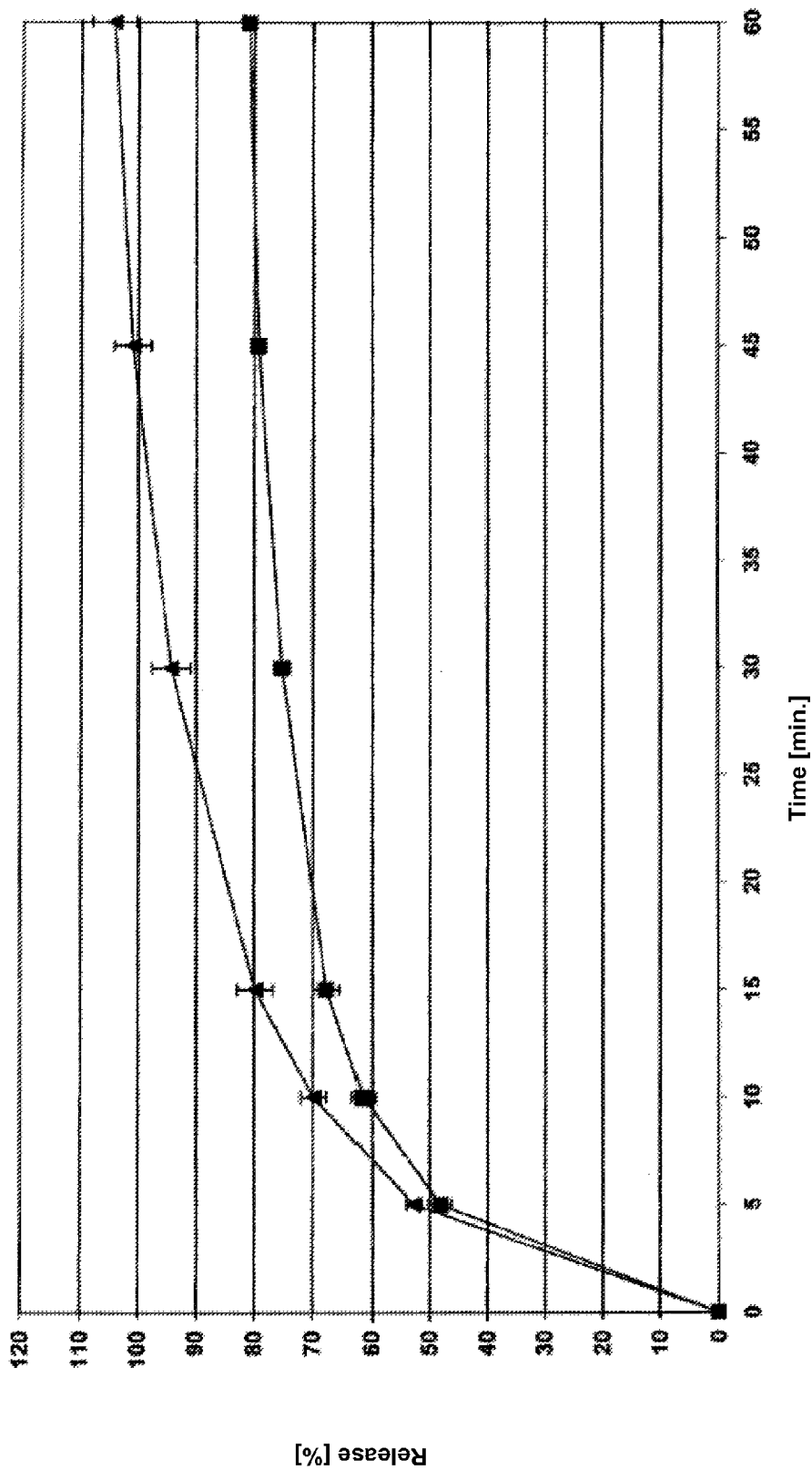
Figure 8:
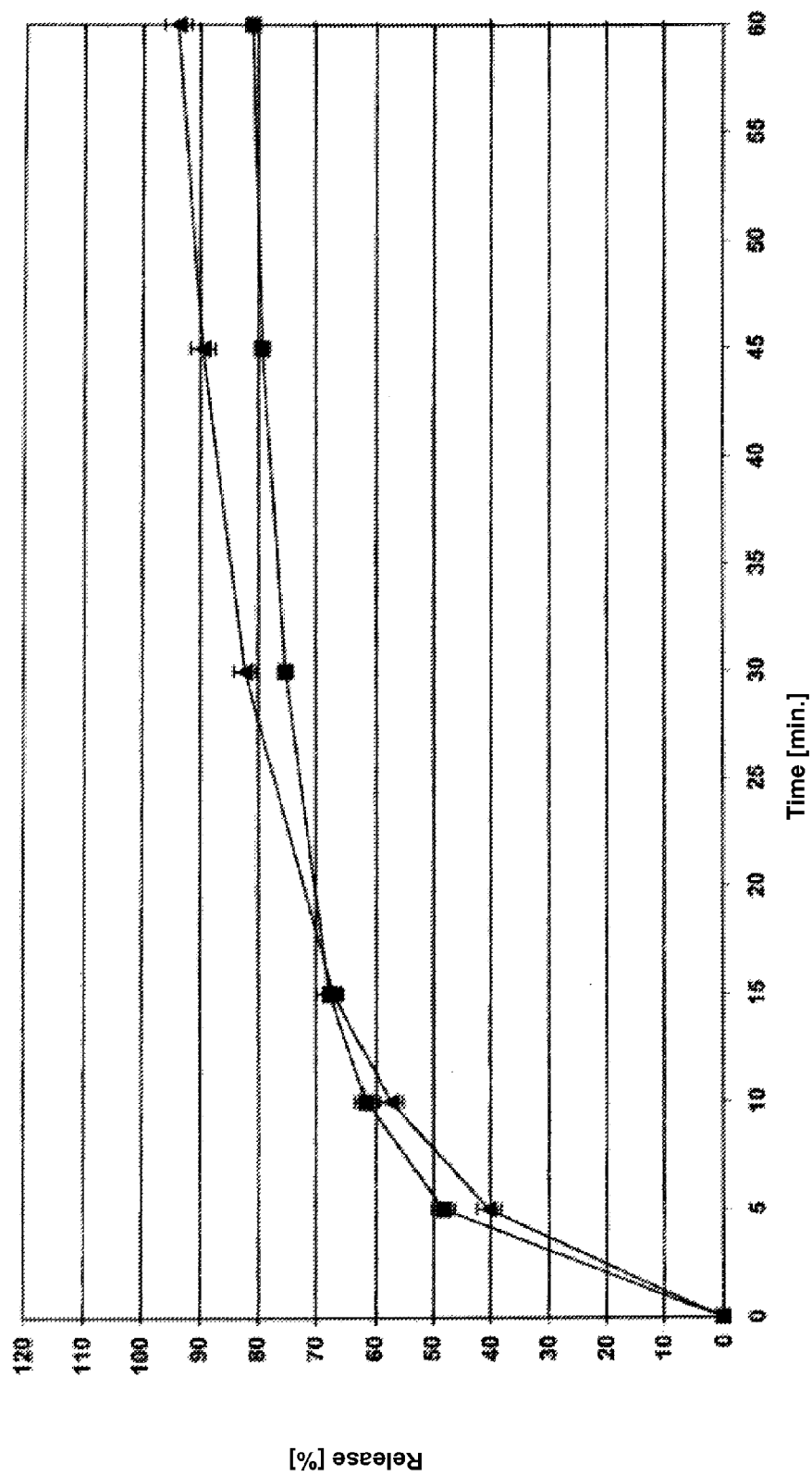
Figure 9:
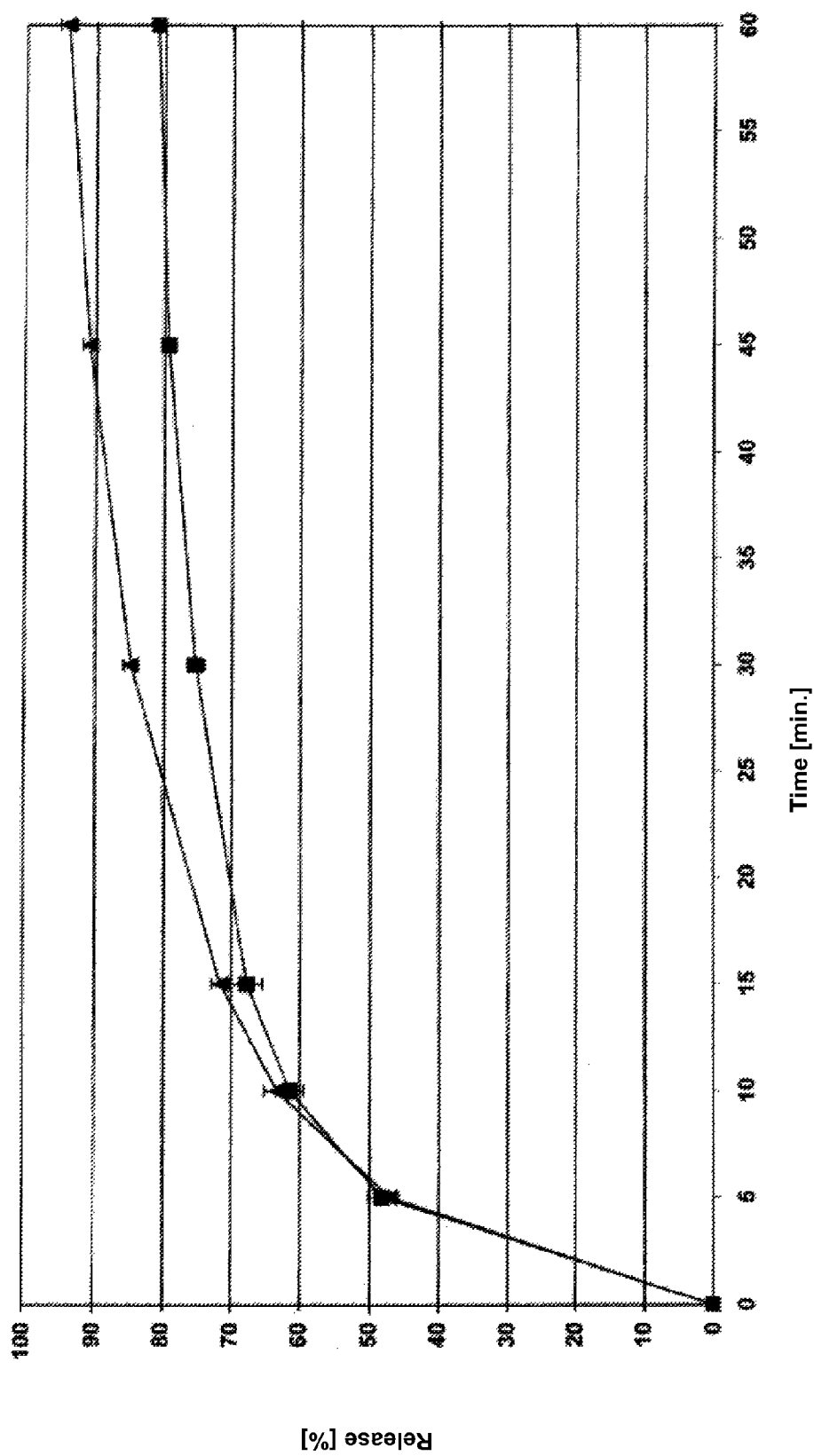
Figure 10:
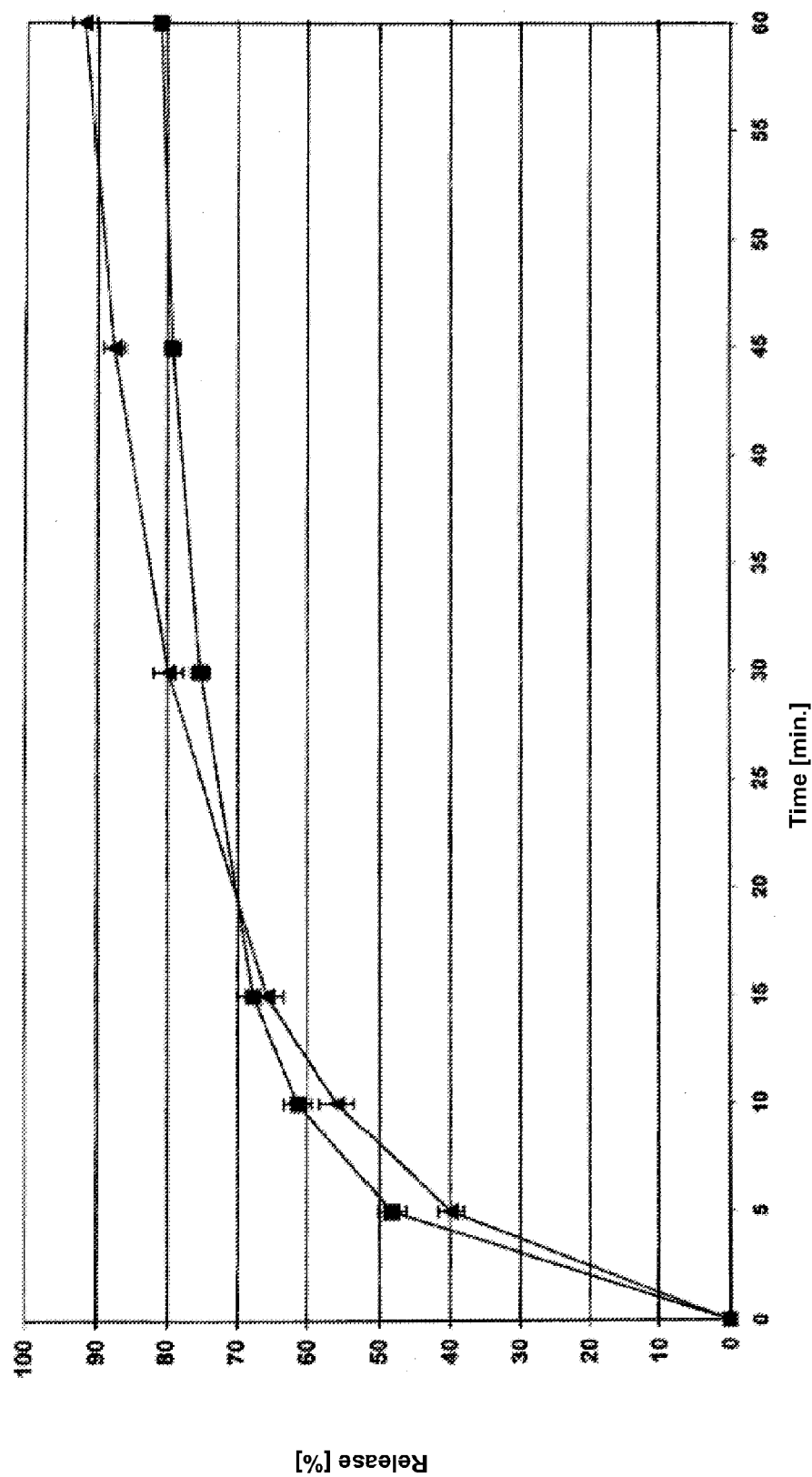
Figure 11:
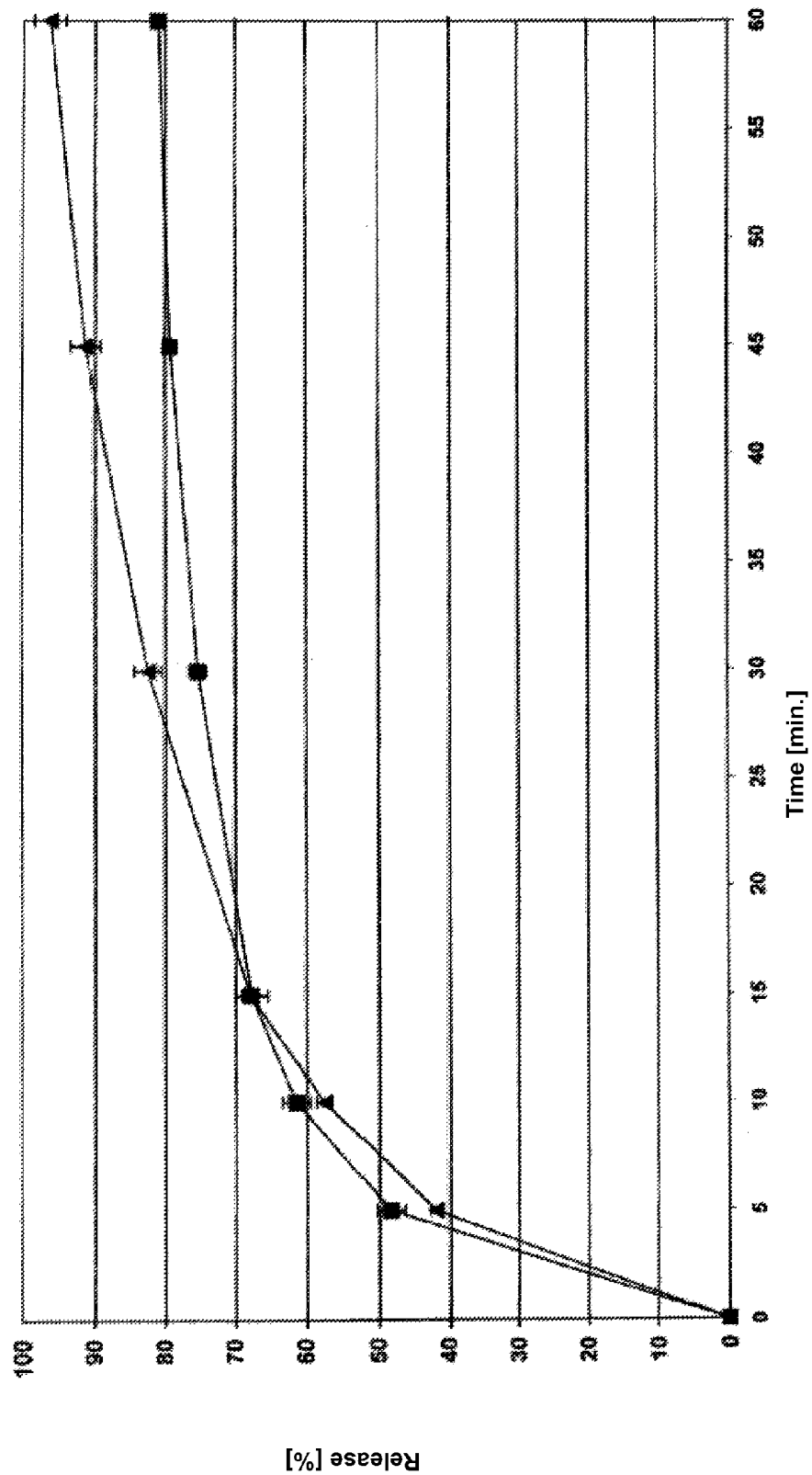

FIG. 3 shows the release profile of the formulation of example 1 (triangles) in comparison to the release profile of the commercial Prasugrel product Efient® (squares), FIG. 4 shows the release profile of the formulation of example 2 (triangles) in comparison to the release profile of the commercial Prasugrel product Efient® (squares), FIG. 5 shows the release profile of the formulation of example 3 (triangles) in comparison to the release profile of the commercial Prasugrel product Efient® (squares), FIG. 6 shows the DSC of the milled composition of example 3, FIG. 7 shows the release profile of the formulation of example 4 (triangles) in comparison to the release profile of the commercial Prasugrel product Efient® (squares), FIG. 8 shows the release profile of the formulation of example 5 (triangles) in comparison to the release profile of the commercial Prasugrel product Efient® (squares), FIG. 9 shows the release profile of the formulation of example 6 (triangles) in comparison to the release profile of the commercial Prasugrel product Efient® (squares), FIG. 10 shows the release profile of the formulation of example 7 (triangles) in comparison to the release profile of the commercial Prasugrel product Efient® (squares), FIG. 11 shows the release profile of the formulation of example 8 (triangles) in comparison to the release profile of the commercial Prasugrel product Efient® (squares).

The present invention is explained in more detail with respect to the following examples without that they should be interpreted to be limiting.

In addition to the active ingredient the following compounds are employed in the examples:

Kollidon VA 64: copolyvinyl pyrrolidone
Pluronic: block copolymers of ethylene oxide and propylene oxide
Avicel: microcrystalline cellulose
HPMC: hydroxypropylmethylcellulose
Kollidon: polyvinyl pyrrolidone
SDS: sodium lauryl sulphate
Acdisol: sodium croscarmellose General methods for the preparation of the formulations
Milling with Ultraturrax (Wet Milling)

In all milling experiments with the Ultraturrax T25 the active ingredient, the polymer, and optionally SDS are dispersed in water for 1 h at 11000 rpm. Thereafter, this suspension is spray dried (Büchi B290; settings=aspirator 70, incoming air 100° C.). The obtained intermediate is then after-dried for 24 h at 30° C. The residual excipients are added, the whole mixture is applied over a 500 μm screen, mixed in a tumbling mixer, and compressed into tablets. Alternatively, in wet milling also the planetary-type ball mill PM100 by Retsch, MicroCer by Netsch, and Koruma Coball Mill MS12 by Fryma may be used.

Milling with the Air Jet Mill 50AS (Dry Milling)

Also here the active ingredient, the polymer, and optionally SDS together are applied over the mill (air jet mill; settings: milling gas=2 bar, injector gas=5 bar). After milling the residual excipients are added, applied over a 500 μm screen, mixed in a tumbling mixer, and compressed into tablets.

EXAMPLE 1

Formulation 1

| Ingredient | mg/tablet | % by weight |
| --- | --- | --- |
| Prasugrel base | 5.00 | 4.23 |
| HPMC 603 | 1.00 | 0.85 |
| Pluronic 127 | 0.25 | 0.21 |
| Acdisol | 12.00 | 10.15 |
| Avicel PH 101 | 100.00 | 84.57 |
| Total weight | 118.25 | 100.00 |

Milling in the Ultraturrax (Wet Milling)

EXAMPLE 2

Formulation 2

| Ingredient | mg/tablet | % by weight |
| --- | --- | --- |
| Prasugrel base | 5.00 | 4.23 |
| HPMC 603 | 1.00 | 0.85 |
| SDS | 0.25 | 0.21 |
| Acdisol | 12.00 | 10.15 |
| Avicel PH 101 | 100.00 | 84.57 |
| Total weight | 118.25 | 100.00 |

Milling in the Ultraturrax (Wet Milling)

EXAMPLE 2a

Formulation 2a

| Ingredient | mg/tablet | % by weight |
| --- | --- | --- |
| Prasugrel base | 5.00 | 4.23 |
| HPMC 603 | 1.00 | 0.85 |
| SDS | 0.25 | 0.21 |
| Acdisol | 12.00 | 10.15 |
| Avicel PH 101 | 100.00 | 84.57 |
| Total weight | 118.25 | 100.00 |

Milling in the Netsch Micro Cer (Wet Milling); Settings:
Wedge-wire screen 0.1 mm; grinding medium 0.2-0.3 mm; speed of the agitator 3000 rpm; pressure of grinding chamber 0.3 bar

EXAMPLE 3

Formulation 3

| Ingredient | mg/tablet | % by weight |
| --- | --- | --- |
| Prasugrel base | 5.00 | 4.23 |
| HPMC 603 | 1.00 | 0.85 |
| SDS | 0.25 | 0.21 |
| Acdisol | 12.00 | 10.15 |
| Lactose Anhydrate | 100.00 | 84.57 |
| Total weight | 118.25 | 100.00 |

Milling in the Ultraturrax (Wet Milling)

The DSC of the milled composition shown FIG. 3 exhibits a sharp peak at 123° C. and thus confirms that the micronized active ingredient is present in the crystalline form.

EXAMPLE 4

Formulation 4

| Ingredient | mg/tablet | % by weight |
|---|---|---|
| Prasugrel base | 5.00 | 4.22 |
| HPMC 603 | 1.00 | 0.84 |
| SDS | 0.25 | 0.21 |
| Vitamin E mixture | 0.20 | 0.17 |
| Acdisol | 12.00 | 10.13 |
| Avicel PH 101 | 100.00 | 84.42 |
| Total weight | 118.45 | 100.00 |

Milling in the Ultraturrax (Wet Milling)

EXAMPLE 5

Formulation 5

| Ingredient | mg/tablet | % by weight |
|---|---|---|
| Prasugrel base | 5.00 | 4.23 |
| Kollidon 30 | 1.00 | 0.85 |
| SDS | 0.25 | 0.21 |
| Acdisol | 12.00 | 10.15 |
| Avicel PH 101 | 100.00 | 84.57 |
| Total weight | 118.25 | 100.00 |

Milling in the Ultraturrax (Wet Milling)

EXAMPLE 6

Formulation 6

| Ingredient | mg/tablet | % by weight |
|---|---|---|
| Prasugrel base | 5.00 | 4.23 |
| HPMC 603 | 1.00 | 0.85 |
| SDS | 0.25 | 0.21 |
| Acdisol | 12.00 | 10.15 |
| Avicel PH 101 | 100.00 | 84.57 |
| Total weight | 118.25 | 100.00 |

Dry Milling with the Jet Mill

EXAMPLE 7

Formulation 7

| Ingredient | mg/tablet | % by weight |
|---|---|---|
| Prasugrel base | 5.00 | 4.23 |
| Kollidon VA64 | 1.00 | 0.85 |
| SDS | 0.25 | 0.21 |
| Acdisol | 12.00 | 10.15 |
| Avicel PH 101 | 100.00 | 84.57 |
| Total weight | 118.25 | 100.00 |

Dry Milling with the Jet Mill

EXAMPLE 8

Formulation 8

| Ingredient | mg/tablet | % by weight |
|---|---|---|
| Prasugrel base | 5.00 | 4.24 |
| Kollidon VA64 | 1.00 | 0.85 |
| Acdisol | 12.00 | 10.17 |
| Avicel PH 101 | 100.00 | 84.75 |
| Total weight | 118.00 | 100.00 |

Spray Drying & Milling in the Ultra Turrax

In all examples the particle size distribution after milling was measured as follows:

| | |
|---|---|
| Instrument | Malvern Mastersizer 2000 with Hydro S |
| Measuring Time | 10 sec. |
| Number of Samples | 3 |
| Background | 10 sec. |
| Model | Fraunhofer |
| Darkenings | approx. 5 |
| Mixing rate | 2500 rpm |
| Ultrasonic Treatment | 50% |
| Ultrasonic Time | 60 sec. |
| Sample Preparation | 50 mg in HPLC Water + one drop of Tween 80; 5 minutes Ultrasonic Treatment |

The following particle size distributions were measured:

In Milling with the Ultraturrax (Wet Milling):
D90: 15.7 μm
D50: 3.4 μm

In Milling with the Netsch Mill (Wet Milling):
D90: 0.2 mm
D50: 0.15 μm

In Milling with the Jet Mill (Dry Milling):
D90: 6.1 μm
D50: 2.2 μm

EXAMPLE 9

Stability Studies

Water Content (According to Karl-Fischer)

| | Start | 2 weeks | 4 weeks |
|---|---|---|---|
| Formulation 3 | 1.30 | 0.90 | 1.00 |
| Efient | 1.50 | 1.60 | 2.00 |

Decomposition (in %):

| | Start | 2 weeks | 4 weeks | 8 weeks |
|---|---|---|---|---|
| Efient | 0.47 | 0.51 | 0.55 | 0.78 |
| Formulation 7 | 0.28 | 0.33 | 0.50 | 0.67 |
| Formulation 3 | 0.42 | 0.53 | 0.53 | 0.72 |

EXAMPLE 10

Release

The release profiles were measured in 900 ml of 50 mM acetate buffer (pH 4.5) at 37° C. and 75 rpm according to the USP method (App. II).

The release profiles of the formulations of examples 1-8 are represented in the FIGS. 3-5 and 7-11 each together with the release profile of the commercial Prasugrel product Efient®. It can be seen that the compositions according to invention in comparison to the commercial Prasugrel product provide a faster release of the active ingredient. Moreover, it is shown from the examples 9 and 10 that the hygroscopicity of the pharmaceutical composition and also the degradation of the active ingredient in the pharmaceutical formulation are reduced in comparison to the commercial Prasugrel product.

The invention claimed is:

1. A composition comprising a micronized, crystalline form of a Prasugrel base.

2. The composition according to claim 1, wherein the micronized, crystalline form of Prasugrel base has a volume-weighted average particle diameter D50 ranging from 0.1 to 10 μm.

3. The composition according to claim 1, wherein the micronized, crystalline form of Prasugrel base has a volume-weighted average particle diameter D90 ranging from 0.2 to 20 μm.

4. The composition according to claim 1, further comprising a hydrophilic polymer.

5. The composition according to claim 4, wherein the weight ratio of the Prasugrel base to hydrophilic polymer is greater than 1:4.

6. The composition according to claim 4, wherein the hydrophilic polymer is selected from the group consisting of cellulose derivatives, polyvinylpyrrolidone, copolymers of polyvinylpyrrolidone, polyoxyethylene alkylether, polyethylene glycol, co-block polymers of ethylene oxide and propylene oxide, polymethacrylate derivatives, polyvinyl alcohol, polyvinyl derivatives and polyethylene glycol derivatives.

7. A method for the preparation of the composition according to claim 4, said method comprising the step of milling the Prasugrel base with a hydrophilic polymer.

8. The method according to claim 7 wherein milling step is carried out as wet or dry milling.

9. The method according to claim 7 wherein milling step is dry milling carried out under cooling.

10. The method according to claim 7 wherein milling step is dry milling carried out in an air jet mill.

11. The method according to claim 10 wherein dry milling is carried out in an air jet mill for a period of at least 30 minutes.

12. A pharmaceutical composition comprising a micronized, crystalline form of Prasugrel base in combination with one or more pharmaceutically acceptable excipients.

13. The composition according to claim 6, wherein the hydrophilic polymer is a cellulose derivative selected from the group consisting of hydroxypropylmethylcellulose, hydroxypropylcellulose, carboxymethylcellulose, and hydroxyethylcellulose.

14. The composition according to claim 13, wherein the hydrophilic polymer is calcium or sodium salt of carboxymethylcellulose.

15. The composition according to claim 6, wherein the hydrophilic polymer is a copolymer of polyvinylpyrrolidone comprising vinylpyrrolidone and vinylacetate units.

16. The method according to claim 10 wherein dry milling is carried out in an air jet mill for a period of at one hour.

* * * * *